United States Patent [19]
Schneider et al.

[11] Patent Number: 5,653,994
[45] Date of Patent: Aug. 5, 1997

[54] COMPOSITION AND METHODS FOR TREATING BURNS AND OTHER TRAUMA OF THE SKIN

[76] Inventors: Norman S. Schneider, 1475 Luning Dr., San Jose, Calif. 95118; Jakob Cherepakho; Elizabeth Cherepakho, both of 1828 Duvall Dr., Apt. 8, San Jose, Calif. 95130

[21] Appl. No.: 481,221

[22] Filed: Jun. 7, 1995

Related U.S. Application Data

[63] Continuation of Ser. No. 143,494, Oct. 25, 1993, abandoned

[51] Int. Cl.⁶ .................................................. A61F 13/00
[52] U.S. Cl. ..................... 424/445; 424/446; 424/447; 424/982; 424/DIG. 13
[58] Field of Search .............................. 424/445, 446, 424/447, 682, DIG. 13

[56] References Cited

U.S. PATENT DOCUMENTS

| | | | |
|---|---|---|---|
| 2,890,987 | 6/1959 | Hilfer | 424/682 |
| 3,098,790 | 7/1963 | Leiter | 424/682 |
| 3,658,984 | 4/1972 | Kamp | 424/28 |
| 3,761,590 | 9/1973 | Fox, Jr. | 424/228 |
| 4,331,653 | 5/1982 | Brown | 424/682 |
| 4,837,019 | 6/1989 | Georgalas | 424/101 |
| 4,868,161 | 9/1989 | Roberts | 514/49 |
| 4,994,497 | 2/1991 | Pepper | 424/DIG. 13 |
| 5,009,890 | 4/1991 | DiPippo | 424/195.1 |

OTHER PUBLICATIONS

American Hospital Formulary Service, 1989, Gerald K. McEvoy, Ed. pp. 1535–1536.

Lawrence, J.C. Burn Bacteriology During the Last 50 Years Excerpt from Supplement 2:1992 50 Years of Burn Wound Care vol. 18 Burns the Journal of the International Society for Burn Injuries.

*Primary Examiner*—D. Gabrielle Phelan
*Attorney, Agent, or Firm*—Fliesler, Dubb, Meyer & Lovejoy

[57] ABSTRACT

A method and composition is provided for treating burns, allergies, trauma or disease of the dermis, epidermis, mucous membranes and subcutaneous tissue, in particular the trauma caused by burns. The method includes applying an aqueous solution of Hydrogen Peroxide ($H_2O_2$) and certain Aluminum salts of carboxylic acids to the trauma, assuring sufficient time of contact of the solution to the affected area of the skin to greatly enhance the healing process. Sufficient contact has been achieved by applying a bandage moistened with the solution to the area of the skin requiring treatment and keeping the bandage moistened for the term of the treatment. An adequate term of treatment has been measured in as little a time as repeated periods of minutes for a period of one day. Success has also been achieved by immersing the treatment area in the aqueous solution. The method provides effective antibacterial activity without undesirable side effects, speedy healing through all phases of cure, significant reduction or elimination of scarring and disfigurement. The method also exhibits significant local anesthetic effect.

15 Claims, No Drawings

COMPOSITION AND METHODS FOR TREATING BURNS AND OTHER TRAUMA OF THE SKIN

This application is a File Wrapper Continuation of Ser. No. 08/143,494, filed Oct. 25, 1993, now abandoned.

BACKGROUND—FIELD OF INVENTION

This invention describes an aqueous based solution, and topical methods of applying the solution which is effective in the healing and alleviation of pain of trauma to the dermis, epidermis, mucous membranes and subcutaneous tissue, in particular to injury caused by heat or chemicals but efficacy is also indicated in the treatment of allergies and other wounds or diseases of the skin. The substances employed are very inexpensive.

BACKGROUND—DESCRIPTION OF THE RELATED ART

Disease of or trauma to the dermis, epidermis, mucous membranes and subcutaneous tissue can result in infection, pain and itching, and disfigurement the form of scarring. Healing of disease or trauma of the dermis, epidermis, mucous membranes and subcutaneous tissue takes variable periods of time depending upon a large number of factors sometimes taking months to heal. The quality of healing of disease or trauma to the dermis, epidermis, mucous membranes and subcutaneous tissue ranges from undetectable to gross disfigurement. Pain experienced by a victim of a burn is a subjective phenomena. Some victims are less impacted by pain than others and some are better able to endure it.

The history of treatment of disease or trauma to the skin is as old as mankind. A vast number of substances have been incorporated in dressings to treat burns and other skin afflictions. Up until the period following the Second World War, very little real progress was achieved in improving burn treatment. The reason for the lack of success is attributable to the extreme complexity of both the antecedent conditions leading up to the trauma followed by the subsequent condition of the patient and the patient's environment. Baron Guillaume Dupuytren, 1777–1835, is quoted in highly sophisticated medical journals ". . . burns so far from being a simple disease are very complex; and their numerous and various degrees constitute affections which present distinct characters, various consequences, peculiar complications and which consequentially require very different modes of treatment." It is not surprising that the many substances applied to wounds or burns to achieve beneficial effect have had varying degrees of success.

Describing the phases or aspects of the healing process for burns aids in understanding the reason for variable results. The healing process for a burn consists of four aspects or phases, Inflammation, Granulation, Epithelialization and Maturation. At each aspect or phase, there are diverse and competing chemical and physical processes occurring in the trauma zone. Application of an external stimulus, such as a dressing to a burn wound, to be effective, must augment or improve the chemical and physical processes needed to enhance healing. Examples of the chemical and physical properties of a substance used in dressings are its chemical composition, its concentration, its pH, its buffering capacity, its biological activity, its osmotic pressure, its volatility, its stability or lack of thereof, its viscosity, its surface tension, its toxicity or lack thereof, its solubilizing effect on body substances, its solubility or lack thereof in its inert vehicle and its catalytic activity or reaction enhancing or inhibiting impact. There are other physical, chemical or pharmacological properties that can have impact on the efficacy of a topical treatment substance.

The Inflammation phase of a burn injury follows immediately the trauma incident. The complex phenomena that occurs in this phase consists of activity by the body's natural healing efforts. These efforts include the fibrin deposition and accumulation of activated platelets on the wound surface. This phenomena produces a matrix for trapping bacteria and other foreign material. Low levels of fibrin and an associated substance, fibronectin, has been shown to increase the risk of septicemia in burn patients. Septicemia and other adverse bacteriological activity is a major factor in the failure of rapid healing of burns.

During the Inflammation phase, the body attempts to influence vasodilation and increased vascular permeability. These are factors which aid the body's natural mechanisms to transport increased quantities of erythocytes to the trauma site. Erythocytes are the oxygen bearing components of red blood cells. In addition, a number of inflammatory mediators, such as histamine, 5-hydroxy tryptamine, kinins, prostaglandins and xanthine oxidase products, which all have an important role in the control of vasodilation and vascular permeability, appear. Also appearing in the Inflammation phase are a number of cytokines such as transforming growth factor beta (TGF-b), insulin like growth factor 1 (IGF-1), platelet factor IV, platelet derived growth factor (PDGF) and epidermal growth factor (EGF). These cytokines attract and activate macrophages and fibroblasts.

The microenvironment of a wound or burn is hostile. It is anoxic, acidic and has high lactate and low glucose levels. This is due to reduced oxygen delivery by a compromised vascular system and increased oxygen consumption by phagocytes and bacteria. The anoxia acidosis and high lactate levels can increase greatly if infection supervenes.

The Granulation, Epithelialization and Maturation phases of healing of burn trauma involve, successively in time, complex chemical and physical activity by the body's defense mechanisms. Some of the chemical and physical activity is closely related or similar to that occurring during the Inflammation phase. Some are different. All phases of healing can be enhanced by the application of appropriate treatment.

Given the extremely complex set of physical and chemical circumstances existing in the burn trauma, it is not surprising that many substances used singly or in combination can have a beneficial effect on one or more of the aspects of healing. Determining a combination of topically applied substances that possess a broad spectrum of beneficial impact on burn and wound trauma is akin to finding the needle in the haystack.

At present the state of the art treatment for many burns is the application of an ointment of silver sulfadiazine, a relatively insoluble silver compound. This material greatly minimizes but does not completely eliminate some toxic side effects of treatment with silver compounds. In addition, systemic absorption may result in the same toxic manifestations as seen with any systemic sulfonamide. It is a greasy substance with the disadvantages associated with such materials. It is inherently expensive because of the silver and sulfadiazine components of the compound. Efficacy of silver sulfadiazine on trauma other than burns is not indicated or claimed. Contact with moisture to the area of trauma is regarded as beneficial in reducing loss of body fluids at the injury site. It is also a factor in reducing pain. Elimination of moisture has been necessary to avoid other serious complications associated with water soluble silver compounds.

Other methods of treating burns exhibit a host of combinations of disadvantages. Leaving an injury open to the air without any medication aids in the mechanical aspects of burn treatment. Debridement, the removal of destroyed tissue is enhanced, but bacterial invasion and loss of bodily fluids by drying is increased. Use of other dressings is often a problem in that the requirement for changing of the dressing is accompanied by pain and disturbance of the scab formation process.

SUMMARY OF THE INVENTION

It is an object of this invention to provide a composition and methods for treating burns and other trauma or disease of the dermis, epidermis, mucous membranes and subcutaneous tissue which possesses superior anti-bacterial activity without undesirable side effects, speeds healing through all phases of cure, eliminates or reduces scarring and disfigurement, exhibits significant pain alleviation, is inexpensive and is easily applied in a variety of ways. The burn treatment method encompassed in this invention consists of the application of an aqueous solution to the trauma.

The solutions that are the subject of this invention consist of aqueous solutions containing Hydrogen Peroxide ($H_2O_2$) and Aluminum esters of the formula $AlOH(R)_2$ and $Al(R)_3$ where R can be a monocarboxylic group of the general formula RCOOH or a dicarboxylic group of the general formula $R(COOH)_2$ or hydroxy carboxylic acids such as glycolic acid ($HOCH_2COOH$) and lactic acid ($CH_3CHOHCOOH$). R is an appropriate organic species suitable as a means of solubilizing the Aluminum ion. Examples of monocarboxylic groups exhibiting an appropriate level of solubilizing capacity are HCOO, the formate, $CH_3COO$, the acetate, $CH_3CH_2COO$, the propionate, and $CH_3(CH_2)_2COO$, the butyrate. Examples of dicarboxylic groups exhibiting an appropriate level of solubilizing capacity are $(COO)_2$, the oxalate, $CH_2(COO)_2$, the malonate, $(CH_2)_2(COO)_2$, the succinate, $(CH_2)_3(COO)_2$, the glutarate and the acetotartrate $((CH_3COO)(CHOHCOO)_2)$. The preferred embodiment of this invention employs a solution whose initial composition by weight is water ($H_2O$) at 98.91%, Hydrogen Peroxide ($H_2O_2$) at 0.27%, and Aluminum Subacetate ($AlOH(CH_3COO)_2$) at 0.82%.

The preferred practice of this invention involves the moistening of a bandage or dressing with an effective amount of the aqueous solution and applying the bandage or dressing to the trauma for an effective period of time. Best results have been achieved when a plastic film exhibiting reduced permeability to water vapor has been placed around the surface of the bandage or dressing. The purpose of the film is to inhibit moisture evaporation, thus keeping the wound in contact with a continuous and consistent concentration of water and the other ingredients. The film also reduces the frequency with which the bandage or dressing must be changed. Another bandage or covering should be placed above the plastic film. It is believed that the second layer of bandage insulates the area of the skin being treated, to keep the wound warm. However, the beneficial effects of this invention have been realized when, absent the plastic film, the bandage or dressing was changed with a frequency sufficient to prevent total drying of the solution. The pain alleviation effect of this treatment is more pronounced when the bandage or dressing is not allowed to dry out completely. Successful treatment has been realized when the solution has been applied to the disease or trauma without the bandage or the bandage covered by a moisture barrier film. The degree of success is related to the frequency and amount of such application.

Individuals have asserted, in all cases, that pain was significantly alleviated by the treatment in accordance with this invention. This invention describes a treatment with an aqueous solution which exhibits unexpected and profoundly beneficial impact on all the adverse effects of disease or trauma to the dermis, epidermis, mucous membranes and subcutaneous tissue. The subject materials of this invention meet that criteria.

The description above contains specific examples. They should not be construed as limiting the scope of the invention. Their purpose is merely to provide the presently preferred embodiments of this invention. For example, there are certainly many additional mono and dicarboxylic organic groups and mixtures of them, not specifically cited, which can fulfill the role of solubilizing the Aluminum ion and providing the appropriate chemical and physical transport of the Hydrogen Peroxide and the Aluminum ion to the trauma active sites.

Therefore the scope of the invention should be determined by the appended claims and their legal equivalents, rather than by the examples given.

Upon further study of the specification and appended claims, further objects and advantages of this invention will become apparent to those skilled in the art.

DETAILED DESCRIPTION OF THE INVENTION

The examples described in this specification took place over a time period when the available Aluminum Subacetate employed underwent changes in concentration. The users of the method of this invention were initially unaware of the variation. As a result the composition of the treatment solution underwent, what amounted to, inadvertent variation.

In the examples described below, the concentration of Aluminum Subacetate varied as did the concentration of Hydrogen Peroxide. The Hydrogen Peroxide varied between 0.23% and 0.27%. The Aluminum Subacetate concentration varied between 0.69% and 2.18%. The ratio of Aluminum Subacetate to Hydrogen Peroxide varied between 3 to 1 and 8 to 1. Other variations in the concentrations of the Aluminum Subacetate occurred but they could not be quantified and are not presented as examples.

Despite the concentration variations in the instances not specifically cited as an example, the use of an aqueous solution of the Aluminum salts in conjunction with Hydrogen Peroxide always exhibited beneficial results in the treatment of burns and other disease of the epidermis, dermis and mucous membranes. Success was achieved with lower and higher concentrations of both ingredients than is exemplified by the preferred embodiment of this invention.

An important result was achieved when a solution of the Aluminum salt and Hydrogen Peroxide was incorporated in a bandage and the bandage was covered with a plastic film. Typically the plastic film employed was the vinyl material available at any grocery store used to bag fruits and vegetables. The plastic film had the property that significantly slowed the evaporation of the water and Hydrogen Peroxide. But, it did not stop the evaporation entirely. The net physical result was that it could take between eight (8) and twenty four (24) or more hours for the solution to evaporate. In that period of time, the concentration of the Aluminum salt increased. Its concentration passed through the level now believed to be the preferred embodiment of this invention. As a consequence, the time the burn was exposed, at or near, to the more effective level of Aluminum salt and Hydrogen Peroxide concentration, was significantly increased.

Wide variation of the conditions of treatment of trauma with the method of this invention is possible given the availability of wide varieties of dressings and plastic films. Certainly those skilled in the art can, with reasonable experimentation, optimize treatment duration at a variety of concentration profiles. The following tables illustrate examples of the duration and concentration profiles that can be applied to the trauma by controlling the initial concentration of the Aluminum salt and the evaporation rate. The evaporation rates chosen in these tables are illustrative of the range believed to have been experienced in practice.

Concentration as a Percent
versus
Time at Selected Evaporation Rates
Evaporation Rates as a % of Solution

| Time Hours | One % Per Hour | Two % Per Hour | Four % Per Hour | Eight % Per Hour |
| --- | --- | --- | --- | --- |
| 0.00 | 0.2000 | 0.2000 | 0.2000 | 0.2000 |
| 4.00 | 0.2082 | 0.2168 | 0.2354 | 0.2790 |
| 8.00 | 0.2167 | 0.2350 | 0.2770 | 0.3890 |
| 12.00 | 0.2256 | 0.2547 | 0.3260 | 0.5421 |
| 16.00 | 0.2348 | 0.2761 | 0.3836 | 0.7551 |
| 20.00 | 0.2444 | 0.2993 | 0.4513 | 1.0509 |
| 24.00 | 0.2544 | 0.3288 | 0.5384 | 1.4008 |
| 0.00 | 0.8000 | 0.8000 | 0.8000 | 0.8000 |
| 4.00 | 0.8325 | 0.8667 | 0.9406 | 1.1132 |
| 8.00 | 0.8664 | 0.9390 | 1.1056 | 1.5471 |
| 12.00 | 0.9016 | 1.0172 | 1.2991 | 2.1464 |
| 16.00 | 0.9383 | 1.1019 | 1.5260 | 2.9708 |
| 20.00 | 0.9764 | 1.1936 | 1.7918 | 4.0987 |
| 24.00 | 1.0161 | 1.3101 | 2.1319 | 5.4081 |
| 0.00 | 2.1800 | 2.1800 | 2.1800 | 2.1800 |
| 4.00 | 2.2674 | 2.3592 | 2.5568 | 3.0170 |
| 8.00 | 2.3582 | 2.5526 | 2.9967 | 4.1616 |
| 12.00 | 2.4526 | 2.7616 | 3.5096 | 5.7150 |
| 16.00 | 2.5506 | 2.9870 | 4.1066 | 7.8010 |
| 20.00 | 2.6525 | 3.2303 | 4.8000 | 10.563 |
| 24.00 | 2.7583 | 3.5386 | 5.6778 | 13.644 |

If a solution of an Aluminum salt were administered to the surface of a wound on the skin without any covering, it evaporates in minutes. Therefore, the initial concentration of the Aluminum salt can be quite low and still achieve the result of effective treatment. The table illustrates that at very low evaporation rates, the one percent (1%) per hour rate, concentration is increased by twenty-five percent (25%) in a twenty-four (24) hour period. At the eight percent (8%) per hour rate, concentration is increased by seven hundred percent (700%) in a twenty-four hour period. There is of course a great number of initial concentrations coupled with evaporation rates that would yield an effective concentration of the active ingredients on the surface of a wound. If the further parameter consisting of applying a newly prepared dressing at various time intervals was added, then a very large number indeed of initial concentrations would be possible to achieve effective treatment. Coupling the mathematical reasoning above with actual observation, it is reasonable to conclude that effective treatment could easily be achieved if the initial concentration of the aluminum salt was initially at a minimum of 0.1% and a maximum of 6.0%. This does not rule out efficacy at lower and higher concentrations.

Hydrogen Peroxide boils at a much higher temperature than water. Therefore, when a dilute aqueous solution of Hydrogen Peroxide evaporates, the concentration of Hydrogen Peroxide will initially increase. As the mixture evaporates the concentration of the mixture will ultimately approach an equilibrium state which is a function of temperature, pressure and most importantly a function of the vapor-liquid equilibrium that exists between water and Hydrogen Peroxide.

Using the similar mathematical reasoning coupled with actual observation as employed in the determination of the effective initial concentration for the Aluminum salt, effective treatment could be achieved if the initial concentration of the Hydrogen Peroxide was initially at a minimum of 0.028% and a maximum of 1.7%.

The preferred embodiment of this invention employs a solution whose initial composition by weight is water ($H_2O$) at 98.91%, Hydrogen Peroxide ($H_2O_2$) at 0.27%, and Aluminum Subacetate ($AlOH(CH_3COO)_2$) at 0.82%.

Preferred practice employs the use of a dressing with the following attributes. The dressing consists of five layers. The first layer contacting the injured area of the skin is standard surgical gauze. The second layer is standard surgical cotton wool. The third layer is a plastic film. The fourth layer can be the same standard surgical cotton wool employed in the first layer. The fifth layer can be the same surgical gauze employed in the first layer.

The first layer of the dressing is made by folding several layers of surgical gauze to a thickness ranging from 1/16 to 3/16 of an inch. It is important to keep this bandage layer as clean and as sterile as possible. Prior to its application to the wound it should be saturated with the treatment solution by dipping it into a source of the solution. Upon removal from the source of solution, the gauze should be squeezed moderately. The squeezing should be of such magnitude that the gauze is wet to the touch, but is not dripping wet.

The first layer of the dressing should be sized to cover the entire area of the wound plus suitable overlap. Suitable overlap varies with the size of the injury being treated. For example, a one square inch wound would be adequately covered by a dressing measuring 2 inches on each side. Very large wounds should be bandaged with a dressing which provides up to 1 inch of overlap on all sides of the injury.

The second layer consisting of surgical cotton fulfills the important function of providing a reservoir of the treatment solution such that the wound is assured of being kept moist for some hours. The treatment solution should be administered to the cotton to a point approaching saturation by dipping the cotton in a source of the solution. Upon removal from the solution, the cotton should be squeezed to exude excess treatment solution. The second layer should be between ½ and ¾ of an inch thick before being somewhat compressed in place by the application of the third, fourth and fifth layers. If the appropriate measure of treatment solution is contained in the surgical cotton wool, only a small mount of the solution will be exuded when the second layer of the dressing is applied to the wound. The degree of compression should be such that the second layer is compressed at most to approximately 70 to 90 percent of its initial height.

The third or middle layer employed was a thin film of polyvinyl chloride (PVC). Such film is traditionally employed in grocery stores to package fruit, vegetables, meat etc. Its thickness is usually one to four mils. Its purpose is two fold. The first is to act as a media for inhibiting evaporation of the treatment solution from the wound area. The second is to retain the second and first layer's position on the wound. Other commercially available films are expected to be suitable substitutes. Since the role of the third layer in the construction of the dressing is physical and mechanical, and not chemical or pharmacological, many media could be substituted to inhibit moisture evaporation and to retain the position of the first two layers. In fact using many of today's space age polymeric building materials, such as polyurethane insulating foam, it is easy to anticipate that a more efficient construction to accomplish the combined function of the third, fourth and fifth layers of this dressing might be invented.

There are available a number of non adhering surgical dressings that are commercially available. One such dressing is the fluorocarbon dressing described below in example 11. Another innovation that may be successfully employed in the practice of this burn treatment method is Saran wrap as the film inhibiting evaporation of moisture. This material was also used in example 11.

The function of the fourth and fifth layers of the dressing is predominantly mechanical. Its purpose is to hold layers one, two and three in place and to provide a measure of insulating value to keep the wound warm. Other materials can easily be substituted which can accomplish the desired result. The thickness of the fifth or outer layer of the dressing is typically that of a cloth bandage. The thickness of the fourth layer should be approximately ¼ to ½ inch. The best mode of constructing the dressing may be difficult to practice on small wounds. Satisfactory treatment results can still be accomplished. Dressings may be constructed using less surgical cotton wool. They will require more frequent changing to assure moisture retention. It may also be necessary to wrap a greater area than the wound itself to conform to the geometry of the body.

The method of application and subsequent reapplication will accomplish the best results if the following methodology is practiced. Each layer of the bandage should be placed in position with a minimum of pressure. Each layer from the wound surface outward should be successively larger than the layer preceding to provide modest overlap. The final layer should be affixed with just enough pressure to keep the layers below from shifting position. Generally the dressing, if applied as described, will perform its function satisfactorily for 12 to 24 hours.

Reapplication of the dressing at suitable intervals is important to achieving optimum results. Most importantly, the dressing should be reapplied whenever it is suspected that the solution is near to drying out. If the dressing is allowed to dry out, a significantly detrimental condition can occur. The dried out surgical gauze in contact with the wound can adhere to the wound. This adherence to the wound can cause serious discomfort to the patient and it can reduce efficacy of the treatment.

Determination of the optimum time for reapplying a freshly moistened dressing to a wound requires experimentation and observation. The caregiver should check the status of the moisture level at periodic intervals to assure that it is not dried out. The patient can also be of great help in ascertaining the reapplication requirement. It has been observed that when the dressing requires reapplication of solution, the patient experiences a feeling akin to the sensation of pinching in the wound area. It is the anesthetic effect which is being impaired. As soon as this observation is made, it can be indicative that too long a period has transpired since the prior moistening of the dressing. Whenever the suspicion exists that the dressing has dried out too much, great care should be exercised in removing the old dressing prior to applying a new dressing. The care is necessary so as to minimize undesired debridement of scab, exudate or injured skin.

It has been determined that the solution that is the subject of this invention is a useful substance to employ in removing a bandage that has adhered to a wound. The solution softens and dissolves the material sticking to the bandage. The solution can be poured onto the dressing adhering to the wound and with gentle mechanical action, the adhering bandage can be removed with minimal undesirable effect.

There are certain other factors relevant to achieving the best results with this invention. In general, the sooner that the treatment described by this invention is commenced after a patient experiences the trauma, the better will be the ultimate result. More importantly, it is necessary to effectuate other supplemental treatment depending upon the severity of the trauma and how quickly treatment is commenced.

Whenever the trauma experienced is so severe, that visible blistering or charring occurs, supplemental treatment is necessary. This supplemental treatment consists of careful debridement of the destroyed tissue by competent medical technique. This means that char and blisters should be surgically removed allowing the treatment solution access to the underlying injury. There are burns which are severe enough, that left untreated, they would blister. Prompt treatment with the procedure described in this invention may avoid the blister. However, some interval later the surface skin may still flake off. This degree of severity does not require debridement.

EXAMPLES

The following examples illustrate the methods and scope of this invention:

Example 1

A man was using a kerosene torch in his garage. While holding the torch in his hands it burst into flames. In panic, he ran on the street with the torch in his hands. His hand was burned very badly. It was severely blistered. There was some blackening indicative of third degree burns. A treatment in accord with the following description was commenced two days after the accident.

A mixture of 1 part, by volume, of 3% Hydrogen Peroxide in water, 7 parts, by volume, of water and 3 parts, by volume of 8% Aluminum Subacetate in water was prepared. This resulted in a final solution of water containing approximately 0.27% by weight of Hydrogen Peroxide and approximately 2.18% by weight of Aluminum Subacetate.

A dressing was prepared consisting of surgical gauze folded to form a surface overlapping the burn area by approximately one half inch (½") on all sides. A layer of surgical cotton approximately three quarters (¾") of an inch thick while uncompressed was placed above the gauze. The solution of Hydrogen Peroxide and Aluminum Subacetate was poured over the surgical cotton and gauze to near saturation. A layer of grocery store type vinyl film was placed on the surface of the dressing. The vinyl film was positioned to secure the dressing and was taped in position. The pressure applied by the vinyl film was sufficient to only partially compress the surgical cotton layer. A fourth layer utilizing surgical cotton wool was placed above the vinyl film. Finally, a bandage was wrapped around the dressing to maintain its position on the wound. It was wrapped in a manner to minimize compression of the surgical cotton. The purpose of the fourth layer of surgical cotton was to insulate the treatment area.

The treatment was performed three times a day. It was necessary to assure that the burn solution did not dry out and allow the dressing to adhere to the skin. Significant relief from pain was achieved immediately after the dressing was applied. The hand started to heal. The skin that was burned to the black color started to peel and under it a new rosy skin appeared. The skin began to itch, a sign of a healing wound after a burn. In about three weeks, the hand completely healed. Mobility of the palm and fingers was restored.

Example 2

A three year old girl spilled a glass of boiling hot water on her leg. She was wearing cotton socks when it happened. Her mother immediately removed her socks and applied a treatment to the burned leg. A treatment in accord with the following description was commenced immediately after the accident.

A mixture of 1 part, by volume, of 3% Hydrogen Peroxide in water, 7 parts, by volume, of water and 3 parts, by volume of 8% Aluminum Subacetate in water was prepared. This resulted in a final solution of water containing approximately 0.27% by weight of Hydrogen Peroxide and approximately 2.18% by weight of Aluminum Subacetate. A dressing was prepared consistent with the detailed description presented in EXAMPLE 1.

The child cried from pain for a while, then fell asleep. Twelve hours later, on the following morning, when the compress was removed, there was not a mark on the leg and the child did not evidence any pain or irritation. Immediate application of the treatment resulted in dramatic results.

Example 3

A man of sixteen years overturned a pot containing one and a half liters of boiling soup on his leg. He was wearing pants at the time and he burned the leg affecting about 30 square inches. Half of the burn area developed blisters. He applied a treatment in accord with the following description within two hours.

A mixture of 1 part, by volume, of 3% Hydrogen Peroxide in water, 9 parts, by volume, of water and 3 parts, by volume of 3% Aluminum Subacetate in water was prepared. This resulted in a final solution of water containing approximately 0.23% by weight of Hydrogen Peroxide and approximately 0.69% by weight of Aluminum Substrate. A dressing was prepared consistent with the detailed description presented in EXAMPLE 1.

The dressing was changed every day for two weeks. At about ten days, the burn appeared completely healed. The burn area retained a slightly darker color for a while until it also disappeared.

Example 4

A seven year old boy was burned when another boy in a steam room overturned a pan of hot water on his back. He was treated in accord with the following description.

A mixture of 1 part, by volume, of 3% Hydrogen Peroxide in water, 7 parts, by volume, of water and 3 parts, by volume of 3% Aluminum Subacetate in water was prepared. This resulted in a final solution of water containing approximately 0.27% by weight of Hydrogen Peroxide and approximately 0.82% by weight of Aluminum Subacetate. A dressing was prepared consistent with the detailed description presented in EXAMPLE 1.

His back healed completely in a week.

Example 5

A women was doing a laundry by bringing to a boil a solution of soap, water and clothing in a thirty liter wash container on a large wood burning stove. When the mixture reached the boiling stage, she lifted the container from the stove and accidentally overturned the soap solution on herself. Blisters soon developed on extensive areas of her body. She was hospitalized. At the hospital it was determined that her burns were extremely serious. Seventy percent of her body was burned. Even her face was burned by steam from the soap solution. After ten days in the hospital, her husband, while visiting the hospital, was told that her burns were likely to cause her death. The doctors said there was no hope. At that time she was taken from the hospital by relatives. Upon arrival at home, a treatment in accord with the following description was applied.

A mixture of 1 part, by volume, of 3% Hydrogen Peroxide in water, 7 parts, by volume, of water and 3 parts, by volume of 3% Aluminum Subacetate in water was prepared. This resulted in a final solution of water containing approximately 0.27% by weight of Hydrogen Peroxide and approximately 0.82% by weight of Aluminum Subacetate. A dressing was prepared consistent with the detailed description presented in EXAMPLE 1. The results were dramatically unexpected. In a week her condition was much improved. The treatment was maintained on major portions of her body for several weeks. The result was that at the end of two weeks, it was clear she would survive. Her whole body felt much better; healing was almost complete. After a month, healing was complete. Only a few scars remained. These scars were barely noticeable.

Example 6

A child, seven months old, inserted his hand into a hot teapot. The burn was serious enough that the skin on his hand was peeling off. A treatment with a burn healing solution in accord with the following description was administered twice a day for five days, at which time his hand was healed.

A mixture of 1 part, by volume, of 3% Hydrogen Peroxide in water, 9 parts, by volume, of water and 3 parts, by volume of 3% Aluminum Subacetate in water was prepared. This resulted in a final solution of water containing approximately 0.23% by weight of Hydrogen Peroxide and approximately 0.69% by weight of Aluminum Subacetate. A dressing was prepared consistent with the detailed description presented in EXAMPLE 1.

Example 7

A man received a burn from a contact with unknown chemicals at his place of work. Treatment in accord with the following description for seven days resulted in complete healing.

A mixture of 1 part, by volume, of 3% Hydrogen Peroxide in water, 7 parts, by volume, of water and 3 parts, by volume of 8% Aluminum Subacetate in water was prepared. This resulted in a final solution of water containing approximately 0.27% by weight of Hydrogen Peroxide and approximately 2.18% by weight of Aluminum Subacetate. A dressing was prepared consistent with the detailed description presented in EXAMPLE 1.

Example 8

A woman was rendering animal fat on the stove when the oil ignited. In her efforts to control the fire, both of her hands were very badly burned. After seven days of treatment with a burn healing solution in accord with this invention, her hands healed without any scars. A mixture of 1 part, by volume, of 3% Hydrogen Peroxide in water, 7 parts, by volume, of water and 3 parts, by volume of 8% Aluminum Subacetate in water was prepared. This resulted in a final solution of water containing approximately 0.27% by weight of Hydrogen Peroxide and approximately 2.18% by weight of Aluminum Subacetate. A dressing was prepared consistent with the detailed description presented in EXAMPLE 1.

Example 9

A women had an ulcerated sore that appeared after a visit to a tropical climate. She had it for thirty years. The sore was treated in accord with the following description.

A mixture of 1 part, by volume, of 3% Hydrogen Peroxide in water, 9 parts, by volume, of water and 3 parts, by volume of 3% Aluminum Subacetate in water was prepared. This resulted in a final solution of water containing approximately 0.23% by weight of Hydrogen Peroxide and approximately 0.69% by weight of Aluminum Subacetate. A dressing was prepared consistent with the detailed description presented in EXAMPLE 1.

Example 10

A man had extensive local anesthesia applied to his mouth for performance of dental procedures. He inadvertently bit the inside surface of his mouth. After the anesthesia had worn off and for three days thereafter, the bite wound was painful and exhibited reluctance to heal. The wound was treated in accord with the following description.

A mixture of 1 part, by volume, of 3% Hydrogen Peroxide in water, 9 parts, by volume, of water and 3 parts, by volume of 3% Aluminum Subacetate in water was prepared. This resulted in a final solution of water containing approximately 0.23% by weight of Hydrogen Peroxide and approximately 0.69% by weight of Aluminum Subacetate.

Cotton swabs were dipped in the solution of Hydrogen Peroxide and Aluminum Subacetate. The moistened swabs were applied and held to the mouth wound. Initially, the swabs were applied to the wound for periods of three to five minutes, at twenty to forty minute intervals over the first three or four hours. After that the treatment was applied three to four times per day for three days. Pain relief was significantly evident within less than an hour of the treatment. Pain continued to abate and was eliminated entirely by the second day. The wound healed without further treatment.

Example 11

A man was stirring up a campfire. In the process a small, red hot coal skipped into the inside of his boot. In the several seconds required to remove the coal, a burn of second to third degree in severity developed.

A mixture of 1 part, by volume, of 3% Hydrogen Peroxide in water, 7 parts, by volume, of water and 3 parts, by volume of 3% Aluminum Subacetate in water was prepared. This resulted in a final solution of water containing approximately 0.27% by weight of Hydrogen Peroxide and approximately 0.82% by weight of Aluminum Subacetate.

The injury, which was approximately one (1) centimeter in diameter, was covered with a porous fluorocarbon treated, non adhering dressing. Cotton balls were held in place with a saran film. The cotton balls, which were moistened with the treatment solution dressing, were positioned over the fluorocarbon treated dressing. The cotton balls were moistened with the treatment solution whenever dryness was ascertained. The cotton and fluorocarbon treated dressing were kept in place with ordinary Saran wrap. The treatment was continued for a ten day period.

Progress in healing was monitored by the patient's father, a medical doctor. Wounds of this type and severity would be expected to be very painful. They would generally require one to two months to heal completely. The healing process of this type of wound would be expected to develop a scabrous surface, followed by a debridement phase in which a small pit would develop. The small pit could take many months to heal to the normal surface of the skin. In this instance, with treatment in accord with this invention, the intensity of pain was minimal, complete healing occurred in less than two week's time without any scarring normally associated with such a burn.

Example 12

A man was barbecuing on a gas fired patio grill. The cover had been closed to increase the heat of the ceramic coals. The man raised the grill cover by means of the wooden handle provided for that purpose. After adjusting the food on the grill, he inadvertently started to close the lid by pushing down on the metal lid. Contact with the lid of the grill caused a sizzling sound and immediate whitening of an oval shaped burn area on the fingerprint area of the man's left index finger and his left middle finger. The injury was immediately treated with cold running water. When the injury was removed from the running water, significant pain was experienced.

A solution was hastily prepared with readily available kitchen implements. The solution prepared consisted of two and one half cups of tap water, 3 tablespoons of Aluminum Acetate $(Al(CH_3COO)_3)$ Topical Solution U.S.P. (BUROW'S SOLUTION), 3 tablespoons of Hydrogen Peroxide $(H_2O_2)$ U.S.P. 3% Topical Solution, and 3 tablespoons of commercial dimethyl sulfoxide $((CH_3)_2SO_2)$ water solution. The dimethyl sulfoxide solution was a 99.99% purity diluted to 90% with water at 10%. Subsequent calculations ascertained that the solution was approximately 90.4% water, 1.33% Aluminum Acetate, 0.27% Hydrogen Peroxide, 7.9% dimethyl sulfoxide and 0.09% Boric Acid $(H_3BO_3)$. Boric Acid is a stabilizer present in the Topical Solution U.S.P. (BUROW'S SOLUTION).

The burned fingers were immersed in the solution for five minute intervals every fifteen minutes for two hours. Then the fingers were immersed in the solution for five minutes every hour for four hours. The man retired for the night thereafter. Immersion in the solution resulted in dramatic lessening of the pain. The pain relief persisted though not as successfully when the fingers were not immersed. Pain on the following morning was negligible. The burn which looked initially as if it were going to blister significantly, did not blister at all. Several days later, the oval areas of the burn were still discernible. The area under the skin remained sensitive to touch. Healing was accomplished without any blistering. The injured area on the index finger was more seriously burned than the area on the middle finger. The burned area on the index finger turned somewhat translucent in two weeks time. Eighteen days after the injury, the skin on the index finger flaked off revealing a sound skin surface. The area on the middle finger injury flaked off on the twentieth day after the injury, also revealing a sound skin surface.

When an unusual synergistic effect manifests itself it is difficult to define the scientific mechanism for the unexpected result. Once the desired result is achieved, a catalog of common properties can be assembled. With these common properties, a workable theory of functionality can be developed.

In this invention the notable common properties are; the presence of a peroxide, the presence of an Aluminum salt of an organic acid, a pH in the weak acid range and the need for a reasonable contact time of the mixture with the injury being treated.

It is a known medical fact that the body attempts as part of the healing process to deliver oxygen to an injury site. Experiments with oxygen augmentation have resulted in some beneficial effect. For example, burn injuries have been subjected to hyperbaric oxygen with some modest improvement noted. As a general rule, Hydrogen Peroxide has been known as an effective anti-bactericide. However, its use has been spurned in favor of a variety of broad spectrum antibiotics. The antibiotics have been judged more effective.

Aluminum salts of organic acids have been available for a long time. There use has been as an astringent. They have the property of being a desiccant. They have been employed as a component in embalming processes. Wounds, particularly burns, are known to require moisture. Serious impairment of burn healing is a consequence of excessive drying of the injury. Therefore, it would be counter intuitive to use a substance that would be a desiccant as burn treatment agent.

Burn injury sites are known to be acidic and anoxic. Conventional treatment has attempted to counter these conditions. Many burn treating substances are neutral or basic in pH at levels of 7 to 9. The substances claimed in this patent all exhibit pH in the weak acid range of 3 to 6.

Our theory of the mechanism of the action of this invention embraces the foregoing common properties. We believe that the properties of the Aluminum ion are at the heart of the performance. The Aluminum ion is responsible for inhibiting the migration of moisture from the injury. An equilibrium is established at the treatment site stabilizing cell membrane autolysis, thus preventing cell destruction. The equilibrium is such that passage of the moisture in the treatment solution with its high Hydrogen Peroxide concentration is promoted into the heart of the wound environment. Thus two vital aspects of wound healing are enhanced. Moisture is maintained and anti-bacterial activity is spread intensively throughout the injury.

The solutions that are claimed consist of aqueous solutions containing Hydrogen Peroxide ($H_2O_2$) and Aluminum esters of the formula $AlOH(R)_2$ and $Al(R)_3$ where R can be a monocarboxylic group of the general formula RCOOH or a dicarboxylic group of the general formula $R(COOH)_2$ or alpha hydroxy carboxylic groups of the general formula $R(HOCH_2COO)$. R is an appropriate organic species suitable as a means of solubilizing the Aluminum ion. Examples of monocarboxylic groups exhibiting an appropriate level of solubilizing capacity are HCOO, the formate, $CH_3COO$, the acetate, $CH_3CH_2COO$, the propionate, and $CH_3(CH_2)_2COO$, the butyrate. Examples of dicarboxylic groups exhibiting an appropriate level of solubilizing capacity are $(COO)_2$, the oxalate, $CH_2(COO)_2$, the malonate, $(CH_2)_2(COO)_2$, the succinate, $(CH_2)_3(CO_0)_2$, the glutarate and the acetotartrate $((CH_3COO)(CHOHCOO)_2)$ or alpha hydroxy carboxylic groups derived from acids such as glycolic acid ($HOCH_2COOH$) and lactic acid ($CH_3CHOHCOOH$).

In addition to Hydrogen Peroxide, there are other soluble pharmacologically acceptable per oxides and other soluble anti-bactericidal materials which can be carried to the internals of the wound by the action of the Aluminum salt.

Pharmacologically active substances which are applied topically have been formulated in a variety of ways to promote ease of application. Such formulations are hydrophillic and hydrophobic. It is expected that the materials claimed will find ready utilization in hydrophillic formulations. These will include lotions, aerosol sprays, toothpastes and mouthwashes. Those skilled in the art will find other means of delivery to the treatment The manufacture of Aluminum Acetate ($Al(CH_3COO)_3$) and Aluminum Substrate ($AlOH(CH_3COO)_2$) is described to insure enabling of this invention. Many of the examples cited in this patent employed material manufactured in accord with the following process. Others employed material manufactured in the United States.

In the first step an aqueous solution of Potassium Aluminum Sulfate salt $Al_2(SO_4)_2K_2SO_4 \cdot 24H_2O$ is reacted with a slurry of finely crushed Calcium Carbonate ($CaCO_3$). The Potassium Aluminum Sulfate salt is commonly known as kalinite. The Calcium Carbonate commonly known as Calcite reacts with the Potassium Aluminum Sulfate salt precipitating a mixture of Calcium Sulfate and Aluminum Hydroxide. Gaseous Carbon Dioxide ($CO_2$) is evolved during the reaction. The combination of the two precipitates can be repeatedly washed with water and filtered to remove soluble impurities, in particular, Potassium Sulfate ($K_2SO_4$).

In the second step, the mixture of washed precipitates are then reacted with Acetic acid ($CH_3COOH$). The Aluminum Hydroxide reacts with the acetic acid to form either Aluminum Acetate or Aluminum Subacetate. Both these salts are quite soluble in the aqueous reaction medium. The Calcium Sulfate is relatively insoluble. The Aluminum salt solution may then be separated from the Calcium Sulfate residue by filtration. The acetate which is formed is a function of the proportion of Acetic acid employed. The process as described employs 39 parts of diluted acetic acid to form Aluminum Subacetate. If Aluminum Acetate were to be the desired end product, the dilute Acetic acid would be increased to 58.5 parts.

The first step of the reaction is conducted in a well stirred jacketed reaction vessel to which 46.5 parts of Potassium Aluminum Sulfate salt and 600 parts of water are added. The reaction vessel should be sized so that the solution occupies less than two thirds of the reactor vessel volume. This is necessary so that when Calcium Carbonate slurry is added the evolution of Carbon Dioxide gas will not cause the vessel contents to surge out of the vessel. The contents of the reaction vessel should be brought to and maintained at ninety degrees centigrade (90° C.) during the reaction phase. In a separate vessel a slurry of 14.5 parts of Calcium Carbonate with 24.5 parts of water is prepared. This mixture should be transferred slowly to the reaction vessel. The speed of addition is dictated by two constraints. The first constraint is that the transfer should be slow enough to prevent the vessel contents from overflowing as Carbon Dioxide evolves as a product of the reaction. The second constraint is that the transfer should be slow enough to allow the contents of the reaction vessel to be kept at approximately ninety degrees centigrade (90° C.) by suitable heating and cooling means.

After the Calcium Carbonate slurry addition is completed, the stirring is stopped and the mixture of precipitates is allowed to settle. The supernatant liquid is removed by decantation. The precipitate mixture is reslurried with water and stirring is resumed. The stirring is stopped, the supernatant liquid is again decanted and the precipitate mixture is again reslurried. This process is repeated as often as necessary to assure that the precipitate is washed free of residual unreacted Potassium Aluminum Sulfate or Potassium Sulfate. Upon completion of the washing process, the slurry of Aluminum Hydroxide and Calcium Acetate precipitates should be passed through a suitable filtering device which permits recovery of the mixed precipitate.

In the second step of the process, the mixed precipitate from the first step is transferred to second vessel. Acetic acid, which has been diluted to a thirty percent (30%) concentration in water, will be added to the mixed precipitates in the amount of 39 parts. This phase of the process should be conducted at a temperature of ten to twelve degrees centigrade (10° C. to 12° C.). Temperature control is important because there are competing reactions taking place between the Acetic acid and the Aluminum Hydroxide. There are three possible Aluminum Acetate salts which can be formed. Two of the salts are soluble They are Aluminum Acetate ($Al(CH_3COO)_3$), sometimes designated as the normal salt and Aluminum Subacetate ($AlOH(CH_3COO)_2$), sometimes designated as the basic salt. The third, ($Al(OH)_2CH_3COO$), a twice substituted salt or dibasic salt as it is sometimes designated is relatively insoluble. Once the dibasic salt is formed, it is difficult and time consuming to convert it back to the normal or basic salt. The second step reaction takes place over a period of two to three days to reach equilibrium. The second step reaction is judged complete by testing the specific gravity of the reaction solution. The assay of the product can be adjusted to the desired composition by the addition of more Acetic acid or of mixed precipitate. Once the assay of the solution is within the desired range, the solution is filtered from the residual precipitate of Calcium Sulfate, the other component of the mixed precipitate.

It is important to comment that the solution that is the subject of this invention can contain small amounts of dissolved Calcium Sulfate ($CaSO_4$), and the dibasic salt, ($Al(OH)_2CH_3COO$). Admittedly, the concentrations of these salts, due to their limited solubility, is very small. The chemical, physical, pharmacological and physical phenomena that takes place in a wound environment is very complex. Many substances are present in minute quantities. It is not possible to define the exact synergy that explains the dramatic performance of this invention. Adequate disclosure requires that the chemistry of this invention be as completely defined as possible.

Chemistry involving Aluminum compounds is complex in that Aluminum exhibits amphoteric behavior. Aluminum compounds can react with both Hydrogen ($H^+$) and Hydroxyl ($OH^-$) ions in solution. Aluminum compounds can sometimes behave as a covalent organic compound.

Other methods of manufacture of the Aluminum salts which are the subject of this invention are employed in the United States. The manufacturing processes employed in the United States differ in that they employ purer raw materials. One such process starts with pure Aluminum Sulfate ($Al_2(SO_4)_3$) and pure Calcium Carbonate. Another process starting with dry food grade Aluminum Hydroxide Gel is also a feasible manufacturing route. Several Aluminum salts which are the subject of this invention are sold commercially in the United States. Among these are Aluminum Subacetate Topical Solution (U.S.P.), Aluminum Acetate Topical Solution (U.S.P.) and Aluminum acetotartrate Solution The term "treatment" as expressed in this patent and as claimed is intended to encompass each one of the following objectives individually and each possible combination of all of them. Treatment means accomplishing the goals of promoting broad spectrum anti-bacterial activity without undesirable side effects, enhancing the curing process in terms of speed of healing, eliminating or reducing scarring and disfigurement compared with other burn treatment procedures, and providing significant alleviation of pain associated with the injury being treated. Disease or trauma as claimed is intended to encompass the plain "Webster's New World Dictionary" definition.

What is claimed is:

1. A method of treating burned tissue of a mammal, comprising, applying a dressing which has been moistened with an aqueous solution of Hydrogen Peroxide and an Aluminum salt of a carboxylic acid, the solution comprising the Hydrogen Peroxide and the Aluminum salt at a ratio of between about 1:3 to about 1:8, to the burned tissue in an amount effective to treat the burned tissue.

2. The method according to claim 1, wherein the Aluminum salt is selected from the group consisting of $AlOH(R)_2$ wherein R is selected from the group consisting of HCOO, $CH_3COO$, $CH_3CH_2COO$, $CH_3(CH_2)_2COO$, $HOCH_2COO$, and $CH_3CH(OH)COO$.

3. The method according to claim 1, wherein the Aluminum salt is selected from the group consisting of $Al(R)_3$ wherein R is selected from the group consisting of HCOO, $CH_3COO$, $CH_3CH_2COO$, $CH_3(CH_2)_2COO$, $HOCH_2COO$, and $CH_3CH(OH)COO$.

4. The method according to claim 1, wherein the Aluminum salt is selected from the group consisting of $AlOH(R)_2$ wherein R is selected from the group consisting of $(COO)_2$, $CH_2(COO)_2$, $(CH_2)_2(COO)_2$, $(CH_2)_3(COO)_2$ and $(CHOHCOO)_2$.

5. The method according to claim 1, wherein the Aluminum salt is selected from the group consisting of AlR1R2 wherein R1 is selected from the group consisting of HCOO, $CH_3COO$, $CH_3CH_2COO$, $CH_3(CH_2)_2COO$, $HOCH_2COO$, and $CH_3CH(OH)COO$ and R2 is selected from the group consisting of $(COO)_2$, $CH_2(COO)_2$, $(CH_2)_2(COO)_2$, $(CH_2)_3(COO)_2$ and $(CHOHCOO)_2$.

6. The method according to claim 1, wherein the Aluminum salt is a mixture of salts ($Al(R)_3$ and $AlOH(R)_2$ wherein R is selected from the group consisting of HCOO, $CH_3COO$ $CH_3CH_2COO$, $CH_3(CH_2)_2COO$, $HOCH_2COO$ and $CH_3CH(OH)COO$.

7. The method according to claim 1, wherein the Aluminum salt is Aluminum Subacetate.

8. The method according to claim 1, wherein the Aluminum salt is Aluminum Acetate.

9. The method according to claim 1, wherein the Aluminum salt is a mixture of Aluminum Acetate and Aluminum Subacetate.

10. The method according to claim 1, wherein the concentration of the Hydrogen Peroxide is between 0.028 per cent and 1.70 per cent by weight and the concentration of the Aluminum salt is between 0.10 per cent and 6.00 per cent by weight.

11. The method according to claim 1, wherein the concentration of the Hydrogen Peroxide is initially at least 0.1 per cent by weight and the concentration of the Aluminum salt is initially at least 0.82 per cent by weight.

12. The method according to claim 1, further comprising covering the dressing with a media that inhibits evaporation of the aqueous solution.

13. The method according to claim 1, wherein the burned tissue is periodically wetted with the aqueous solution.

14. The method according to claim 1, wherein the aqueous solution is incorporated in a hydrophilic formulation.

15. A method of easing the release of dressings which have adhered to the skin of an animal, comprising contacting the dressing with a release easing effective amount of an aqueous solution of Hydrogen Peroxide and an Aluminum salt of a carboxylic acid.

* * * * *

UNITED STATES PATENT AND TRADEMARK OFFICE
CERTIFICATE OF CORRECTION

PATENT NO. : 5,653,994
DATED : August 5, 1997
INVENTOR(S) : Norman S. Schneider, et al.

It is certified that error appears in the above-indentified patent and that said Letters Patent is hereby corrected as shown below:

On the cover page under "Attorney, Agent, or Firm" after "Fliesler Dubb, Meyer & Lovejoy", please insert -- ; John Q. LeKashman --.

Signed and Sealed this

Sixteenth Day of December, 1997

Attest:

BRUCE LEHMAN

Attesting Officer

Commissioner of Patents and Trademarks